United States Patent [19]
Yang et al.

[11] Patent Number: 5,948,315
[45] Date of Patent: Sep. 7, 1999

[54] SUNLIGHT-ULTRAVIOLET-STABLE BIOCIDE COMPOSITIONS AND USES THEREOF IN WATER TREATMENT

[75] Inventors: Shunong Yang; William F. McCoy, both of Naperville, Ill.

[73] Assignee: Nalco Chemical Company, Naperville, Ill.

[21] Appl. No.: 09/059,901

[22] Filed: Apr. 14, 1998

[51] Int. Cl.⁶ .............................. C02F 5/02; A01N 25/00; A01N 59/08; A01N 59/22
[52] U.S. Cl. .......................... 252/175; 424/405; 424/661; 424/663; 424/667; 424/672; 514/602; 514/603; 514/604
[58] Field of Search ...................................... 252/180, 181, 252/175; 514/602, 603, 604; 564/84; 424/405, 661, 663, 667, 672

[56] References Cited

U.S. PATENT DOCUMENTS

| | | | |
|---|---|---|---|
| 3,328,294 | 6/1967 | Self et al. | 210/62 |
| 3,493,654 | 2/1970 | Goodenough et al. | 424/127 |
| 3,558,503 | 1/1971 | Goodenough et al. | 252/187 |
| 3,767,586 | 10/1973 | Ruthiewic | 252/187 |
| 4,642,194 | 2/1987 | Johnson | 210/699 |
| 4,711,724 | 12/1987 | Johnson | 210/699 |
| 4,759,852 | 7/1988 | Trulear | 210/699 |
| 4,992,209 | 2/1991 | Smyk et al. | 252/387 |
| 5,439,611 | 8/1995 | Sherbondy et al. | 252/180 |
| 5,449,476 | 9/1995 | Sherbondy et al. | 252/180 |
| 5,589,106 | 12/1996 | Shim et al. | 252/387 |
| 5,683,654 | 11/1997 | Dallmier et al. | 424/14 |

OTHER PUBLICATIONS

Talanta, vol. 27, pp. 669–670, 1980; "Bromamine–B as a New Oxidimetric Titrant", M. Sayeed Ahmed and D.S. Mahadevappa.

International Journal of Chemical Kinetics, vol. 28, pp. 873–878, 1996; "Oxidation of Some Primary Amines by Bromamine–B in Alkaline Medium: A Kinetic and Mechanistic Study", S. Ananda, T. Demappa, D.S. Mahadevappa and N.M. Made Gowda.

Journal of Physical Organic Chemistry, vol. 2, pp. 660–671, 1989; "Oxidation of Substituted Ethanols by Sodium N–Bromobenzenesulphonamide: A Kinetic Study", Puttaswamy and D.S. Mahadevappa.

Encyclopedia of Chemical Technology, vol. 24, pp. 427–441, 3rd ed., Kirk Othmer.

*Primary Examiner*—Jose' G. Dees
*Assistant Examiner*—Alton Pryor
*Attorney, Agent, or Firm*—Kelly L. Cummings; Thomas M. Breininger

[57] ABSTRACT

A sunlight-ultraviolet-stable biocide composition for use in treating recreational and industrial water systems is disclosed which comprises an oxidizing halogen compound and a stabilizer, wherein the stabilizer is either benzenesulfonamide or a derivative thereof.

27 Claims, No Drawings

SUNLIGHT-ULTRAVIOLET-STABLE BIOCIDE COMPOSITIONS AND USES THEREOF IN WATER TREATMENT

FIELD OF THE INVENTION

This invention relates generally to biocides and, more particularly, to sunlight-ultraviolet-stable biocide compositions for use in treating recreational and industrial water systems.

BACKGROUND OF THE INVENTION

Oxidizing halogen compounds, specifically, chlorine, bromine and iodine are known to degrade in the sunlight-ultraviolet (UV) spectral region (hereinafter referred to as "sunlight-UV").

The sunlight-UV degradation of halogens is a serious problem in swimming pools, spas, and hot tubs and can also be a serious problem in certain industrial water treatment applications, such as decorative fountains, settling and cooling ponds, clarifiers, etc. Without the addition of a proper halogen stabilizer, over 50% of the halogen will decompose in less than half an hour under normal sunlight illumination.

Based on the principles of photochemistry, for an oxidizing halogen compound to be degraded under UV illumination, two process steps must occur. The first step is UV absorption of the molecule by which the molecule is excited to an higher energy state. In the second step, the excited molecule undergoes a photodegradation reaction. By understanding the mechanism of this reaction, two approaches can be taken to prevent a halogen from undergoing photodegradation. The first approach is to look for an oxidizing halogen compound that has minimal light absorption in the UV range (sunlight-UV is from 290 to 400 nm). The second approach is to look for an oxidizing halogen compound which even at the excited state does not undergo a photodegradation reaction, but rather undergoes vibrational relaxation to return to ground state. For example, unstabilized bromine has a maximum absorption at 330 nm. However, a stabilized bromine solution may have different light absorption characteristics depending on the properties of the stabilizer and degree of stabilization. The lower the absorption in UV range, the more stable the bromine will be.

Bromine is known to be an excellent biocide in recreational water treatment. However, the use of bromine has been severely limited in outdoor swimming pools due to its rapid degradation in sunlight-UV. There is no known practical means to protect bromine from such degradation. Therefore, bromine is limited to only about 10% of the specialty biocide market share and is used principally for indoor pools and spas. Bromine is preferred for pool use because antimicrobial performance is superior to chlorine and bromine is less irritating to soft tissues and membranes, such as in and around the eyes. U.S. Pat. No. 3,493,654 (Goodenough et al.) describes the use of succinimide as a stabilizer to increase the half-life of bromine in UV illumination. However, although some UV stability is achieved, none of the stabilizers disclosed in the Goodenough et al. patent are used commercially because they are either not practical or effective enough.

Currently, degradation of chlorine, but not bromine, can be substantially prevented in sunlight-UV by using an organic stabilizer such as triazine-s-trione (cyanuric acid). Commercially, chloroisocyanurate is the principal specialty biocide used in pools for microbiological control (approximately 90% of the specialty biocide market share) because the cyanurate stabilizer protects chlorine from degradation by sunlight-UV. However, cost is a factor because, to be effective, large amounts of the cyanurate stabilizer are required. Typically, at least 35 parts per million (ppm) of cyanurate must be used for every 1 ppm of chlorine.

According to the Kirk Othmer Encyclopedia of Chemical Technology, Third Edition, Wiley Interscience, Volume 24, pages 427–441, the recommended initial cyanuric acid concentration is 50 ppm. However, if the concentration goes above 100 ppm, partial drainage of the pool water and refilling with fresh water will be required because the excessively high cyanuric acid concentration may slow down the rate of disinfection. Therefore, the operational window for cyanuric acid is quite narrow (a concentration factor of 2).

Accordingly, it would be desirable to develop a biocide composition for use in treating recreational and industrial water systems which is sunlight-UV stable, economically-appealing and has a wide operational window.

SUMMARY OF THE INVENTION

The biocide composition of the present invention comprises an oxidizing halogen compound and a stabilizer, wherein the stabilizer is either benzenesulfonamide or a derivative thereof.

The inventive biocide composition is sunlight-UV stable, economically-appealing and has a wide operational window for use in treating recreational and industrial water systems.

DETAILED DESCRIPTION OF THE INVENTION

The present invention is directed to a sunlight-UV-stable biocide composition for use in treating recreational and industrial water systems. The biocide composition comprises an oxidizing halogen compound and a stabilizer.

The oxidizing halogen compounds which may be used in the practice of this invention are oxidizing chlorine, bromine and iodine compounds. The oxidizing chlorine compounds which may be employed include chlorine, hypochlorite, hypochlorous acid, chlorinated isocyanurates and chloroamines. The oxidizing bromine compounds which can be used herein are bromine, hypobromite, hypobromous acid, bromine chloride, bromo-chloro-diethylhydantoin, stabilized sodium hyprobromite (available from Nalco Chemical Company under the name STABREX) and bromamines. The oxidizing iodine compounds which may be used are iodine, hypoiodite, hypoiodous acid, iodophores and iodamines.

The stabilizers which may be employed in the practice of this invention include benzenesulfonamide and derivative compounds of benzenesulfonamide, such as 4-nitrobenzenesulfonamide and 4-carboxybenzenesulfonamide. Benzenesulfonamide and 4-nitrobenzenesulfonamide are preferred.

The molar ratio of the stabilizer to the oxidizing halogen compound in the biocide composition is preferably about 0.1:50, more preferably about 1:10, and most preferably about 1:1.

The present inventors have discovered that the inventive biocide composition can be effectively used to inhibit microbial growth in recreational and industrial water systems.

Moreover, the biocide composition has been found to be sunlight-UV stable. This finding is unexpected because other bromine stabilizers, such as sulfamate, are not able to provide protection for bromine from sunlight-UV degradation. The sunlight-UV stability of the biocide composition can be changed by varying the ratio of the stabilizer to the halogen within the range described above.

The types of recreational water systems in which the biocide composition can be utilized include, but are not limited to, indoor and outdoor swimming pools, spas and hot tubs. The oxidizing halogen compound and stabilizer of the biocide composition can be added to the recreational water system by any conventional method either separately or as a composition containing both components.

The types of industrial water systems in which the biocide composition can be employed include, but are not limited to, cooling water systems, settling and cooling ponds, reservoirs, decorative fountains, industrial pasteurizers, evaporative condensers, clarifiers, hydrostatic sterilizers and retorts, gas scrubber systems, air washer systems and wastewater treatment plants. The oxidizing halogen compound and stabilizer of the biocide composition can be added to the industrial water system by any conventional method either separately or as a composition containing both components.

It is preferred that the amount of oxidizing halogen compound which is added to the recreational or the industrial water be in the range of about 0.1 ppm to about 20 ppm. More preferably, the amount of the oxidizing halogen compound is from about 0.2 ppm to about 5 ppm, with about 0.2 ppm to about 1 ppm being most preferred.

It is preferred that the amount of stabilizer which is added to the recreational or the industrial water be in the range of about 0.1 ppm to about 100 ppm. More preferably, the amount of the stabilizer is from about 0.5 ppm to about 50 ppm, with about 1 ppm to about 10 ppm being most preferred.

EXAMPLES

The following examples are intended to be illustrative of the present invention and to teach one of ordinary skill how to make and use the invention. These examples are not intended to limit the invention or its protection in any way.

Example 1

2.14 grams of 50% NaOH were added to 20 ml of water. 2 grams of benzenesulfonamide were then added to the alkaline water and the solution was mixed until the benzenesulfonamide completely dissolved. Liquid bromine was then slowly added to the solution. The resulting biocide composition was 7.2% as $Br_2$ (or 3.18% as $Cl_2$ by DPD-FAS free residual titration according to Standard Method 4500-Cl F) of N-bromo-benzenesulfonamide (NBB) with a pH of 12.8.

Example 2

The biocidal performance of the NBB prepared above in Example 1 was tested against *Pseudomonas aeruginosa* culture at various dosages. The test was performed in a phosphate buffer solution having a pH of approximately 7.5. The contact time between the biocide and the bacteria was 4 hours. The biocidal efficacy of the treatment was determined by the TGE plate count method (Standard Methods for the Examination of Water and Wastewater, 19th ed., Method 9215C) and the results were expressed by the logarithm reduction of the colony formation unit. As shown below in Table 1, there was significant biocidal activity at low dosages. The halogen concentrations were as dosed.

TABLE 1

| NBB Concentration Dosed (ppm as Chlorine) | Log Reduction |
| --- | --- |
| 0.5 | 1.4 |
| 1 | 4.1 |
| 1.5 | 4.7 |
| 2 | 5.1 |

Example 3

A bottle containing the concentrated NBB solution prepared above in Example 1 was put into a 57° C. water bath to test its thermal stability. Samples were withdrawn over a 20-day period to measure the NBB remaining (% as bromine). As shown below in Table 2, the NBB solution was stable at an elevated temperature for an extended period of time.

TABLE 2

| Time (days) | NBB Remaining (% as $Br_2$) |
| --- | --- |
| 0 | 7.70 |
| 2 | 6.62 |
| 8 | 7.04 |
| 13 | 7.25 |
| 20 | 7.40 |

Example 4

UV degradation experiments were conducted in a laboratory UV chamber, equipped with both UVA and UVB lamps, to compare the UV stability of various bromine-based biocides. Various oxidizing halogen compositions were added to 200 ml of ultrapure demand-free water in a 90×50 crystallization dish to achieve a resulting concentration of about 10 ppm (as $Cl_2$). The dish was then put inside a UVA&B chamber for UV illumination. The Iw chamber was constructed according to ASTM standard test method E 896-92. The light intensity on the solution surface was constant at 160 footcandles. One milliliter of sample was then withdrawn from the dish at various time intervals for active halogen concentration determination. The halogen concentration was determined by DPD calorimetric method (Standard Methods for the Examination of Water and Wastewater, 19th ed., Method 4500-Cl G) after 10-fold dilution.

As shown below in Table 3, the UV stability was much greater for the inventive biocide compositions than for the oxidizing bromine compounds, such as hypobromite and STABREX.

TABLE 3

| Bromine source | NaOBr[1] | NaOBr | NaOBr | NaOBr | BCDMH[2] | BCDMH | STABREX[3] | STABREX |
|---|---|---|---|---|---|---|---|---|
| Stabilizer | none | BSAM[4] | CBSAM[5] | NBSAM[6] | none | BSAM | none | BSAM |
| Bromine to stabilizer molar ratio | — | 1:1 | 1:1 | 1:1 | — | 1:1 | — | 1:1 |
| Time of UV exposure (minutes) | Percent of halogen residual remaining (AH residual was measured as free, except STABREX with no stabilizer was measured as total.) | | | | | | | |
| 0 | 100.0 | 100.0 | 100.0 | 100.0 | 100.0 | 100.0 | 100.0 | 100.0 |
| 20 | 72.4 | 94.9 | 92.9 | 97.2 | 92.5 | 92.0 | 76.3 | 88.1 |
| 40 | 67.3 | 90.7 | 90.1 | 89.8 | 79.2 | 84.0 | 57.6 | 81.7 |
| 60 | 61.2 | 86.4 | 83.0 | 87.0 | 67.9 | 78.0 | 44.6 | 77.8 |
| 80 | 55.1 | 81.4 | 78.0 | 80.6 | 62.3 | 70.0 | 38.1 | 73.0 |
| 100 | 48.9 | 76.3 | 69.5 | 75.9 | 52.8 | 68.0 | 30.2 | 69.8 |
| 120 | 40.8 | 72.0 | 66.0 | 74.1 | 41.5 | 64.0 | 24.5 | 65.1 |
| 140 | 36.7 | 66.1 | 59.6 | 72.2 | 37.7 | 62.0 | — | — |
| 150 | — | — | — | — | — | — | 18.0 | 60.3 |
| 160 | 33.7 | 61.9 | 55.3 | 71.3 | 37.7 | 60.0 | — | — |
| 1st order decay rate (1/min) | 0.0073 | 0.0030 | 0.0038 | 0.0023 | 0.0068 | 0.0033 | 0.0113 | 0.0032 |
| Halogen half-life (min) | 95 | 231 | 182 | 301 | 102 | 210 | 61 | 216 |

[1] NaOBr = sodium hypobromite
[2] BCDMH = bromo-chloro-dimethylhydantoin
[3] STABREX = a stabilized sodium hypobromite available from Nalco Chemical Company
[4] BSAM = benzenesulfonamide
[5] CBSAM = 4-carboxybenzenesulfonamide
[6] NBSAM = 4-nitrobenzenesulfonamide Example 5

The same experiments performed above in Example 4 were conducted to evaluate the UV stabilization of chlorine-based biocides. As shown below in Table 4, a 1:1 molar ratio of sodium hypochlorite to benzenesulfonamide provided better protection for chlorine than a 1:20 molar ratio of sodium hypochlorite to cyanuric acid.

TABLE 4

| Chlorine source | NaOCl[1] | NaOCl | NaOCl | NaOCl | NaOCl | NaOCl |
|---|---|---|---|---|---|---|
| Stabilizer | none | CYA[2] | CYA | CYA | BSAM[3] | NBSAM[4] |
| chlorine to stabilizer molar ratio | — | 1:1 | 1:10 | 1:20 | 1:1 | 1:1 |
| Time of UV exposure (minutes) | Percent of halogen residual remaining (All residual was measured as free, except BSAM and NBSAM were measured as total.) | | | | | |
| 0 | 100.0 | 100.0 | 100.0 | 100.0 | 100.0 | 100.0 |
| 20 | 50.4 | 52.3 | 59.6 | 94.4 | 95.1 | 87.7 |
| 40 | 26.4 | 28.4 | 38.4 | 87.9 | 88.9 | 86.0 |
| 60 | 18.6 | 17.1 | 21.2 | 74.8 | 86.4 | 78.9 |
| 80 | 13.2 | 10.2 | 16.2 | 69.2 | 79.0 | 77.2 |
| 100 | 10.1 | 6.8 | 10.1 | 68.2 | 76.5 | 69.3 |
| 120 | 8.5 | 4.6 | 6.1 | 67.3 | 72.8 | 65.8 |
| 140 | 7.0 | 4.6 | 4.0 | 56.1 | 70.4 | 61.4 |
| 160 | 4.7 | 3.4 | 4.0 | 55.1 | 64.2 | 61.4 |
| 1st order decay rate (1/min) | 0.0230 | 0.0212 | 0.0211 | 0.0038 | 0.0031 | 0.0021 |
| Halogen half-life (min) | 30 | 33 | 33 | 182 | 224 | 330 |

[1] NaOCl = sodium hypochlorite
[2] CYA = cyanuric acid
[3] BSAM = benzenesulfonamide
[4] NBSAM = 4-nitrobenzenesulfonamide Example 6

Additional testing was conducted to investigate the effect of excess stabilizer on the biocidal performance of hypobromite. The same bacterial culture was used and a similar testing procedure was followed as in Example 2. Phosphate buffer solution was used as the reaction media. Sodium hypobromite solution was freshly prepared by stoichiometrically reacting sodium bromide with sodium hypochlorite. This solution was used as the oxidizing bromine source. 1% w/w of benzenesulfonamide solution was prepared separately at an alkaline pH condition. The sodium hypobromite and benzenesulfonamide stock solutions were dosed separately into the phosphate buffer solution containing about 1e6 cell per ml of *Pseudomonas aeruginosa*. A portion of the testing solution was then taken at various time intervals for bacterial count determination. The test results are shown below in Table 5.

TABLE 5

| Sample # | 1 | 2 | 3 | 4 | 5 | 6 | 7 |
|---|---|---|---|---|---|---|---|
| Hypobromite dosed (ppm as $Cl_2$) | 0 | 2 | 2 | 2 | 2 | 2 | 2 |
| Molar ratio of benzenesulfonamide to hypobromite | n/a | 0 | 1 | 3 | 5 | 10 | 35 |
| Contact Time (hours) | \multicolumn{7}{c}{Bacterial count (CFU/ml)} | | | | | | |
| 0 | 4.0e6 | 2.5e6 | 2.5e6 | 3.4e6 | 2.3e6 | 2.2e6 | 2.3e6 |
| 0.5 | 2.3e6 | 1.2e3 | 3.3e4 | 2.4e4 | 5.2e4 | 4.4e5 | 1.2e6 |
| 1 | 2.6e6 | 1.2e3 | 1.4e3 | 3.9e4 | 5.9e4 | 1.4e5 | 6.8e5 |
| 2 | 6.3e6 | <100 | 3e2 | 3.1e3 | 2.3e3 | 3.2e4 | 1.9e5 |
| 6 | 4.9e6 | <100 | <100 | <100 | <100 | 6e2 | 9e2 |
| 24 | 3.2e6 | 3e2 | <100 | <100 | <100 | <100 | 2e2 |
| Halogen concentration remaining at 24 hours (ppm as $Cl_2$) | n/a | 0.03 | 0.08 | 0.31 | 0.54 | 0.87 | 1.10 |

As demonstrated above in Example 5, benzenesulfonamide provides excellent sunlight-UV stability for bromine at a 1:1 molar ratio. Therefore, the results shown in Table 5 indicate that the benzenesulfonamide-bromine system has a wide operational window (up to a concentration factor of 10) that does not significantly affect the biocidal performance of bromine. Moreover, because the persistency of the halogen in the test solution improves with the addition of benzenesulfonamide, the application of this stabilizer is even more economically-appealing.

While the present invention is described above in connection with preferred or illustrative embodiments, these embodiments are not intended to be exhaustive or limiting of the invention. Rather, the invention is intended to cover all alternatives, modifications and equivalents included within its spirit and scope, as defined by the appended claims.

What is claimed is:

1. A sunlight-ultraviolet-stable biocide composition consisting of an oxidizing halogen compound and a stabilizer, wherein the stabilizer is selected from the group consisting of benzenesulfonamide and derivative compounds of benzenesulfonamide.

2. The composition of claim 1 wherein the oxidizing halogen compound is selected from the group consisting of oxidizing chlorine, bromine and iodine compounds.

3. The composition of claim 2 wherein the oxidizing chlorine compounds are selected from the group consisting of chlorine, hypochlorite, hypochlorous acid, chlorinated isocyanurates and chloroamines.

4. The composition of claim 2 wherein the oxidizing bromine compounds are selected from the group consisting of bromine, hypobromite, hypobromous acid, bromine chloride, bromo-chloro-dimethylhydantoin, stabilized sodium hypobromite and bromamines.

5. The composition of claim 2 wherein the oxidizing iodine compounds are selected from the group consisting of iodine, hypoiodite, hypoiodous acid, iodophores and iodamines.

6. The composition of claim 1 wherein the stabilizer is benzenesulfonamide.

7. The composition of claim 1 wherein the stabilizer is 4-nitrobenzenesulfonamide.

8. The composition of claim 1 wherein the molar ratio of the stabilizer to the oxidizing halogen compound is about 0.1:50.

9. The composition of claim 1 wherein the molar ratio of the stabilizer to the oxidizing halogen compound is about 1:10.

10. The composition of claim 1 wherein the molar ratio of the stabilizer to the oxidizing halogen compound is about 1:1.

11. A method of inhibiting microbial growth in a water system consisting of the step of adding to the water effective inhibiting amounts of an oxidizing halogen compound and a stabilizer, wherein the stabilizer is selected from the group consisting of benzenesulfonamide and derivative compounds of benzenesulfonamide.

12. The method of claim 11 wherein the oxidizing halogen compound is selected from the group consisting of oxidizing chlorine, bromine and iodine compounds.

13. The method of claim 12 wherein the oxidizing chlorine compounds are selected from the group consisting of chlorine, hypochlorite, hypochlorous acid, chlorinated isocyanurates and chloroamines.

14. The method of claim 12 wherein the oxidizing bromine compounds are selected from the group consisting of bromine, hypobromite, hypobromous acid, bromine chloride, bromo-chloro-dimethylhydantoin, stabilized sodium hypobromite and bromamines.

15. The method of claim 12 wherein the oxidizing iodine compounds are selected from the group consisting of iodine, hypoiodite, hypoiodous acid, iodophores and iodamines.

16. The method of claim 11 wherein the stabilizer is benzenesulfonamide.

17. The method of claim 11 wherein the stabilizer is 4-nitrobenzenesulfonamide.

18. The method of claim 11 wherein the oxidizing halogen compound is added to the water in an amount of from about 0.1 ppm to about 20 ppm.

19. The method of claim 11 wherein the oxidizing halogen compound is added to the water in an amount of from about 0.2 ppm to about 5 ppm.

20. The method of claim 11 wherein the oxidizing halogen compound is added to the water in an amount of from about 0.2 ppm to about 1 ppm.

21. The method of claim 11 wherein the stabilizer is added to the water in an amount of from about 0.1 ppm to about 100 ppm.

22. The method of claim 11 wherein the stabilizer is added to the water in an amount of from about 0.5 ppm to about 50 ppm.

23. The method of claim 11 wherein the stabilizer is added to the water in an amount of from about 1 ppm to about 10 ppm.

24. The method of claim 11 wherein the water system is a recreational water system.

25. The method of claim 11 wherein the water system is a industrial water system.

26. The method of claim 24 wherein the recreational water system is a swimming pool.

27. The method of claim 24 wherein the recreational water system is an outdoor swimming pool.

* * * * *

UNITED STATES PATENT AND TRADEMARK OFFICE
CERTIFICATE OF CORRECTION

PATENT NO. : 5,948,315
DATED : September 7, 1999
INVENTOR(S) : Shunong Yang and William F. McCoy It is certified that error appears in the above-identified patent and that said Letters Patent is hereby corrected as shown below:

Column 4, Line 48 a UVA&B chamber for UV illumination. The Iw chamber should read a UVA&B chamber for UV illumination. The UV chamber Signed and Sealed this Ninth Day of May, 2000

Attest:

Attesting Officer

Q. TODD DICKINSON

Director of Patents and Trademarks